US008105298B2

(12) United States Patent
Mullejans et al.

(10) Patent No.: US 8,105,298 B2
(45) Date of Patent: Jan. 31, 2012

(54) OSTOMY APPLIANCE

(75) Inventors: Peter Mullejans, Aalsgaarde (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 1011 days.

(21) Appl. No.: 10/591,450

(22) PCT Filed: Mar. 1, 2005

(86) PCT No.: PCT/DK2005/000141
§ 371 (c)(1), (2), (4) Date: May 24, 2007

(87) PCT Pub. No.: WO2005/082271
PCT Pub. Date: Sep. 9, 2005

(65) Prior Publication Data
US 2007/0260206 A1  Nov. 8, 2007

(30) Foreign Application Priority Data
Mar. 1, 2004  (DK) .................................. 2004 00343

(51) Int. Cl.
*A61F 5/44* (2006.01)

(52) U.S. Cl. ........ 604/332; 604/336; 604/337; 604/338; 604/339; 604/341; 604/342; 604/343; 604/344

(58) Field of Classification Search .................. 604/333, 604/331–332, 336–339, 341–344
See application file for complete search history.

(56) References Cited

U.S. PATENT DOCUMENTS

| | | | | |
|---|---|---|---|---|
| 2,660,877 A | * | 12/1953 | Malouf | 70/455 |
| 2,708,802 A | * | 5/1955 | Baker et al. | 40/331 |
| 3,089,493 A | * | 5/1963 | Galindo | 604/342 |
| 4,367,732 A | | 1/1983 | Poulsen et al. | |
| 4,449,970 A | | 5/1984 | Bevan et al. | |
| 4,460,363 A | * | 7/1984 | Steer et al. | 604/336 |
| 4,710,183 A | | 12/1987 | Steer | |
| 4,714,465 A | | 12/1987 | Steer | |
| 4,816,027 A | * | 3/1989 | Gilchrist et al. | 604/339 |
| 4,826,495 A | * | 5/1989 | Petersen | 604/333 |
| 5,051,259 A | | 9/1991 | Olsen et al. | |
| 5,209,744 A | | 5/1993 | Abe et al. | |
| 5,306,264 A | | 4/1994 | Ferguson et al. | |
| 5,312,381 A | * | 5/1994 | Brooks | 604/338 |
| 5,423,782 A | | 6/1995 | Wolrich | |
| 5,426,782 A | | 6/1995 | Shiga | |
| 5,496,297 A | | 3/1996 | Olsen | |
| 5,520,670 A | * | 5/1996 | Blum | 604/338 |
| 5,591,144 A | | 1/1997 | Smith et al. | |
| 5,690,622 A | | 11/1997 | Smith et al. | |
| 5,690,623 A | | 11/1997 | Lenz et al. | |
| 5,714,225 A | | 2/1998 | Hansen et al. | |

(Continued)

FOREIGN PATENT DOCUMENTS

CA  1 108 958  9/1981

(Continued)

*Primary Examiner* — Tatyana Zalukaeva
*Assistant Examiner* — Ginger T Chapman
(74) *Attorney, Agent, or Firm* — Jacobson Holman PLLC

(57) ABSTRACT

A disposable inner bag liner for an ostomy appliance, the inner bag liner being adhered to a release liner prior to attachment to an outer receiving member. The release liner includes an alignment element and a gripping element. An ostomy appliance including the aforementioned inner bag liner with the gripping element and/or the alignment element is also provided, along with a method of application of the inner bag liner.

27 Claims, 15 Drawing Sheets

U.S. PATENT DOCUMENTS

Figure 1:
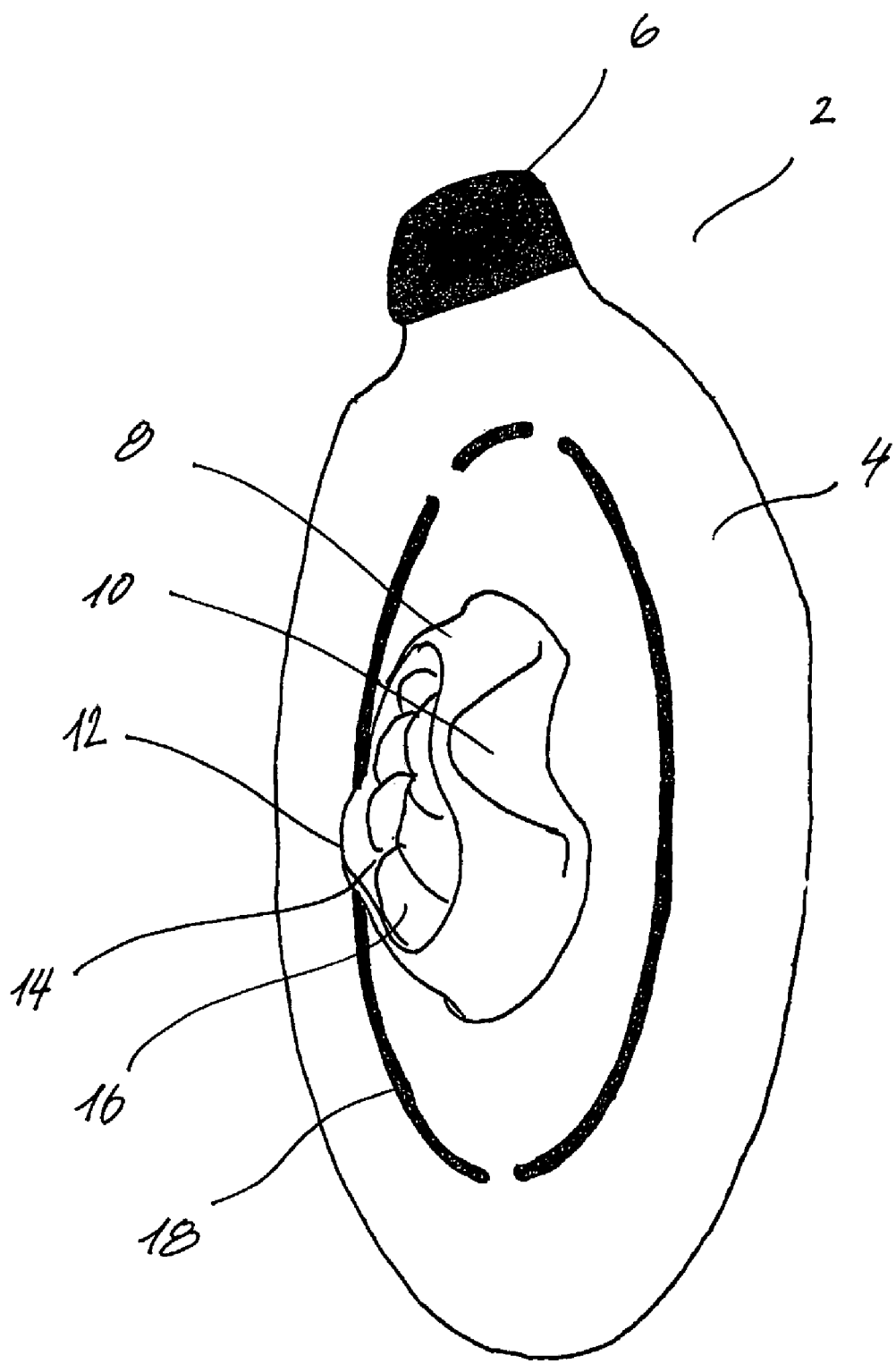

| | | | |
|---|---|---|---|
| 5,785,695 A * | 7/1998 | Sato et al. | 604/339 |
| 5,800,415 A * | 9/1998 | Olsen | 604/336 |
| 5,865,819 A * | 2/1999 | Cisko et al. | 604/339 |
| 5,938,647 A * | 8/1999 | Smith | 604/332 |
| 5,989,235 A * | 11/1999 | Quacquarella et al. | 604/332 |
| 6,171,594 B1 | 1/2001 | Nielsen | |
| 6,303,700 B1 | 10/2001 | Chen | |
| 6,312,415 B1 | 11/2001 | Nielsen et al. | |
| 6,437,038 B1 | 8/2002 | Chen | |
| 6,451,883 B1 | 9/2002 | Chen et al. | |
| 6,685,683 B1 | 2/2004 | Clok et al. | |
| 7,214,217 B2 * | 5/2007 | Pedersen et al. | 604/333 |
| 7,470,263 B2 * | 12/2008 | Strobech | 604/336 |
| 7,604,622 B2 * | 10/2009 | Pedersen et al. | 604/333 |
| 7,722,586 B2 * | 5/2010 | Mullejans et al. | 604/342 |
| 7,819,850 B2 * | 10/2010 | Mullejans et al. | 604/344 |
| 7,931,631 B2 * | 4/2011 | Pedersen et al. | 604/344 |
| 2003/0023210 A1 * | 1/2003 | Bedard et al. | 604/332 |
| 2004/0064132 A1 | 4/2004 | Boehringer et al. | |
| 2005/0113770 A1 * | 5/2005 | Pedersen et al. | 604/332 |
| 2008/0004580 A1 * | 1/2008 | Mullejans et al. | 604/344 |

FOREIGN PATENT DOCUMENTS

| | | |
|---|---|---|
| DE | 1 947 368 | 4/1971 |
| DE | 195 19 069 A1 | 11/1996 |
| DE | 199 21 555 A1 | 2/2000 |
| DE | 203 08 266 U1 | 8/2003 |
| DE | 20 2004 000 323 U1 | 5/2004 |
| EP | 0 259 184 B1 | 3/1988 |
| EP | 0 320 895 A1 | 6/1989 |
| EP | 0 703 762 B1 | 4/1996 |
| EP | 0 747 026 B1 | 12/1996 |
| EP | 0 768 848 B1 | 4/1997 |
| EP | 0 768 849 B1 | 4/1997 |
| EP | 0 821 925 B1 | 2/1998 |
| EP | 1 290 994 A2 | 3/2003 |
| FR | 2 476 481 A1 | 8/1981 |
| GB | 2 265 832 A | 10/1993 |
| GB | 2 306 889 A | 5/1997 |
| HU | 190 848 | 11/1986 |
| WO | WO 91/01118 | 2/1991 |
| WO | WO 91/01119 | 2/1991 |
| WO | WO 93/18725 | 9/1993 |
| WO | WO 94/12128 | 6/1994 |
| WO | WO 94/18919 | 9/1994 |
| WO | WO 96/01090 | 1/1996 |
| WO | WO 99/30652 | 6/1999 |
| WO | WO 00/30576 | 6/2000 |
| WO | WO 00/54820 | 9/2000 |
| WO | WO 00/67683 | 11/2000 |
| WO | WO 01/05340 A2 | 1/2001 |
| WO | WO 01/10363 A1 | 2/2001 |
| WO | WO 01/21115 A1 | 3/2001 |
| WO | WO 01/54632 A1 | 8/2001 |
| WO | WO 01/82846 A1 | 11/2001 |
| WO | WO 02/058603 A1 | 8/2002 |
| WO | WO 2004/082452 A2 | 9/2004 |

* cited by examiner

OSTOMY APPLIANCE

This is a nationalization of PCT/DK2005/000141 filed 1 Mar. 2005 and published in English.

FIELD OF THE INVENTION

The present invention relates to a disposable inner bag liner for an ostomy appliance, the inner bag liner being adhered to a release liner prior to attachment to an outer receiving member. In particular the present invention relates to an alignment means and to gripping means of the release liner.

Additionally the present invention relates to an ostomy appliance comprising the aforementioned inner bag liner with the gripping means and/or the alignment means.

Finally the invention relates to a method of application of the inner bag liner.

BACKGROUND OF THE INVENTION

It is known in the art to provide ostomy appliances having an outer bag and a flushable inner bag. Such an appliance is known from the applicant's own publication WO 01/82846.

Other ostomy appliances may be seen in EP 0 768 848, EP 0 703 762, EP 0 768 848, GB 2 306 889, EP 0 821 925 and U.S. Pat. No. 5,423,782.

It may be seen as an object of the present invention to provide a solution which makes it easier for the user to align a disposable inner bag liner in relation to an outer receiving bag. Especially it may be seen as an object to provide a system making it easier for a disabled person to apply a disposable inner bag correctly.

Additionally it may be seen as an object of the present invention to provide a system making it easy to hold/grip a release liner when applying a disposable inner bag to an outer receiving member.

DESCRIPTION OF THE INVENTION

According to a FIRST ASPECT the present invention relates to a disposable inner bag liner for an ostomy appliance, the inner bag liner being capable of forming a bag inside an outer receiving member, the disposable inner bag liner comprising an open end having an annular first flange comprising: a first hole for receiving a stoma, ureter, or catheter for receiving effluents or waste products of the body, a first surface being provided with an adhesive and a release liner, and a second surface; the outer receiving member comprising: a second hole for receiving a stoma, ureter, or catheter for receiving effluents or waste products of the body, and a second flange; wherein the second flange of the member and the second surface of the liner are adapted to be releasably adhered to each other and wherein the release liner is provided with first alignment means for aligning the first flange in relation to the second flange.

The receiving member may be a bag. The disposable inner bag liner and the receiving member can be adapted to be attached to a base plate which is adapted to be attached to the skin of a user. The first flange and the second flange can in some embodiments be attached to the base plate.

Moreover, the second flange of the receiving member and the second surface of the inner bag liner may be adhered to each other by means of an adhesive provided on the flange and/or the second surface.

In one embodiment the second flange of the receiving member is releasably adhered or attached to a third surface of the base plate. The base plate and/or the second flange may be provided with an adhesive.

The release liner of the present invention may be provided with a first alignment element. One advantage of providing the release liner with such an alignment element is that it is easier to apply the disposable inner bag liner in the correct way in relation to the receiving member, especially for a disabled person.

In a further embodiment the first alignment means may be adapted to align the first hole substantially concentric in relation to the second hole. If the first and/or the second hole are not provided in the centre of the flange the alignment means may be used to make sure that the holes are positioned correctly in relation to each other. Alternatively the first alignment means can be used to align the first flange substantially concentric in relation to the second flange.

In one embodiment the second flange is provided with second alignment means adapted to co-operate with the first alignment means. Such co-operation may be provided by means of magnets or co-operating surfaces etc.

In other embodiments the first alignment means is/are adapted to engage the second alignment means. The first alignment means may engage the second alignment means in at least one point and/or along at least one surface.

In one embodiment the first alignment means of the release liner defines one or more protrusions. Thus when a predetermined part of the second flange abut on the protrusions the first and second flange are aligned correctly.

The first alignment means of the release liner may define a recess and/or hole adapted to by engaged by the protrusions of the second flange. Alternatively the second alignment means defines a recess and/or hole adapted to be engaged by the first alignment means.

The first alignment means of the release liner may define an alignment leg protruding from at least a part of an outer rim of the release liner and in a direction transverse to the first flange or the release liner. Accordingly a part of the alignment leg of the release liner may engage at least a part of an outer rim of the second flange. In one embodiment the alignment leg is provided along the entire rim of the release liner.

The outer leg may alternatively be provided on the first flange.

In one embodiment the second flange has a unique shape which leaves only one way of positioning the second flange of the receiving member in relation to the release liner. As an example the second flange may be provided with one tap extending from a central part of the second flange. Thus if the first flange or the release liner is provided with means to navigate in relation to the tap of the second flange, it may be possible to provide only one possible way of positioning the first flange/release liner in relation to the second flange.

In another example the second flange is provided with a notch in the rim and the release liner and/or the first flange is provided with a protrusion adapted to engage the notch such that the flanges may only be aligned in one specific way.

The alignment leg may protrude along the entire outer rim of the first flange. Alternatively a plurality of legs may be provided along the edge of the release liner.

In one embodiment the alignment means comprises a geometrical shape indicating a corresponding shape of the second flange. Such a geometrical shape could be a figure or a line on the release liner indicating the right position of the release liner in relation to the first flange. Advantageously the release liner is transparent and comprises a line having substantially the same shape as the rim of the second flange or the shape of a recess defined in the second flange. Alternatively the geometrical shape may define a line on the surface of the first flange.

The geometrical shape may protrude from the first flange or from the release liner. The protruding line may protrude in a direction towards the second flange or it may protrude the opposite way. The protruding line may also be used to engage at least a part e.g an edge, of the second flange The invention according to the first aspect may also comprise features and elements described under the second aspect of the invention.

Furthermore, the first aspect may comprise the following features and elements:

Point 1. A disposable inner bag liner according to any combination of features and/or elements of the aforementioned description of the first aspect, wherein the release liner comprises gripping means.

Point 2. A disposable inner bag liner according to point 1, wherein the gripping means protrudes from an outer rim of the release liner.

Point 3. A disposable inner bag liner according to point 2, wherein a gripping plane defined by at least a part of the gripping means is transverse to a liner plane defined by at least a part of the release liner provided inside the outer rim.

Point 4. A disposable inner bag liner according to point 3, wherein the gripping plane and the liner plane defines an angel of between 5 to 45 degrees.

Point 5. A disposable inner bag liner according to any of point 1-4, wherein the gripping means protrudes from a surface of the release liner.

Point 6. A disposable inner bag liner according to point 4, wherein the gripping means defines at least two gripping surfaces to as to allow gripping of the liner with two fingers.

Point 7. A disposable inner bag liner according to any of points 5 or 6, wherein the gripping surfaces are transverse to a liner plane defined by at least a part or the release liner.

Point 8. A disposable inner bag liner according to any of points 5-7, wherein the gripping surfaces are concave.

Point 9. A disposable inner bag liner according to point 8, further comprising a compartment projecting from the liner, the compartment defining the gripping surfaces.

According to a SECOND ASPECT the present invention relates to a disposable inner bag liner for an ostomy appliance, the inner bag being provided with a first surface provided with an adhesive and a release liner, and a second surface being adapted to be attached to at least a part of an outer receiving member, wherein the release liner comprises gripping means.

One gripping means may be provided or a plurality of gripping means may be provided. The gripping means may be shaped so as to have the opposite shape than fingers i.e. a plurality of cavities each being adapted to be engaged by a finger.

The gripping means may be used to ensure correct gripping of the release liner and thus reduce the risk of wrong application of inner bag liner in relation to the receiving member. The gripping means may be provided on any part of the release liner. As an example the gripping means may protrude from the surface of the release liner or it may protrude from an outer rim of the release liner. In the latter example it may be provided as a tap of the release liner.

A gripping plane defined by at least a part of the gripping element may be transverse to a liner plane defined by at least a part of the release liner provided inside the outer rim. If the gripping element is provided as a tap extending from the rest of the release liner, the tap will extend in a direction transverse to the rest of the release liner. The outer receiving bag may further be provided with a corresponding tap extending from a second flange. When the first flange to which the release liner is adhered, is to be brought into contact with the second flange, the two taps may be positioned on top of each other. In this situation the central part of the release liner and the first flange are not in contact with the second flange but extend in a direction transverse to the second flange. Hereafter the first flange and the release liner may be lowered such that the two taps are not in contact and such that the first flange and the second flange are brought into contact. The gripping plane and the liner plane may define an angle of between 5 to 45 degrees, such as 10 degrees, such as 20 degrees, such as 30 degrees, such as 40 degrees. Alternatively it may define an angle of up to 90 degrees.

In another embodiment the gripping means may protrude from a surface of the release liner. In the latter embodiment the gripping means may be provided as a plurality of protruding elements or notches or as one protruding element. The gripping means may define at least two gripping surfaces so as to allow gripping of the liner with two fingers. The gripping surfaces may be provided opposite each other.

The gripping surfaces may be transverse to a liner plane defined by at least a part or the release liner. Furthermore, the gripping surfaces may be concave. In one embodiment a compartment projects from the liner, with the compartment defining the gripping surfaces. The compartment may be adapted to contain the inner bag liner prior to application onto the second flange of the receiving member. When the first flange of the inner bag is adhered to the second flange, the inner bag may be pushed into the outer member through a hole in the compartment.

The compartment defining a gripping area, meaning the outer surface of the compartment, and/or the gripping surfaces may have a primarily circular shape for example with a projecting rim at the distal part of the compartment in relation to the first flange of the inner bag liner for improved gripping of the release liner.

Furthermore, the second aspect may comprise the following features and elements:

Point 10. A disposable inner bag liner according to any combination of features and/or elements of the aforementioned description of the second aspect, wherein the inner bag liner is capable of forming a bag inside an outer receiving member and wherein
  the disposable inner bag liner further comprises an open end having a annular first flange comprising:
    a first hole for receiving a stoma, ureter, or catheter for receiving effluents or waste products of the body,
    the first surface being provided with an adhesive and the release liner, and
    a second surface;
  the outer receiving member comprising
    a second hole for receiving a stoma, ureter, or catheter for receiving effluents or waste products of the body, and
    a second flange;
wherein the second flange of the member and the second surface of the liner are adapted to be releasably adhered to each other and wherein the release liner is provided with first alignment means for aligning the first flange in relation to the second flange.

Point 11. A disposable inner bag liner according to point 10, where in the first alignment means are adapted to align the first hole substantial concentric in relation to the second hole.

Point 12. A disposable inner bag liner according to point 10 or 11, wherein the first alignment means are adapted to align the first flange substantially concentric in relation to the second flange.

Point 13. A disposable inner bag liner according to any of points 10-12, wherein second flange is provided with second alignment means adapted to co-operate with the first alignment means.

Point 14. A disposable inner bag liner according to point 13, wherein the first alignment means is adapted to engage the second alignment means.

Point 15. A disposable inner bag liner according to point 12 or 13, wherein a first alignment surface of the first alignment means is adapted to engage a second alignment surface of the second alignment means.

Point 16. A disposable inner bag liner according to any of points 10-15, wherein the first alignment means defines a protrusion comprising the first alignment surface.

Point 17. A disposable inner bag liner according to any of points 10-16, wherein the first alignment means defines a recess and/or hole adapted to by engaged by the second alignment means.

Point 18. A disposable inner bag liner according to any of points 10-17, wherein the second alignment means defines a recess and/or hole adapted to be engaged by the first alignment means.

Point 19. A disposable inner bag liner according to any of points 10-18, wherein the first alignment means defines an alignment leg protrudes from at least a part of an outer rim of the first flange.

Point 20. A disposable inner bag liner according to point 19, wherein the alignment leg protrudes along the entire outer rim of the first flange.

Point 21. A disposable inner bag liner according to any of points 10-20, wherein the alignment means are comprises a geometrical shape indicating a corresponding shape of the second flange.

Point 22. A disposable inner bag liner according to point 21, wherein the geometrical shape protrudes from the first flange.

Point 23. A disposable inner bag liner according to point 21 or 22, wherein the geometrical shape defines a line on the surface of the first flange.

Point 24. A disposable inner bag liner according to any combination of features and/or elements of the aforementioned description of the second aspect, wherein the closed end of inner bag liner in a compacted state is provided with a cover.

The cover may merely cover the hole in the inner bag liner. However, it may also cover a larger part of the annular first flange of the inner bag as well as the hole, or it may cover a major part of or the entire first flange of the inner bag liner as well as the hole.

Point 25. A disposable inner bag liner according to any combination of features and/or elements of the aforementioned description of the second aspect, wherein the release liner is provided with a protection film placed at the opposite side of the release liner in relation to the cover.

The protection film may be easily penetrated, for example by being providing with at least one perforated line at some distance from the edge of the protection film or by being provided with slits, for example in the shape of a cross.

The invention according to the second aspect may also comprise features and elements described under the first aspect of the invention.

In the following, additional features of the first and second aspect of the present invention are described.

The inner bag liner may be compacted lengthwise to form a disc-like structure having an outer diameter less than an inner diameter of the second hole. Thus, a unit, which is simple to handle is provided which unit may be used with existing ostomy equipment.

The folding of the inner bag liner minimises the risk of "pancaking" and blocking of the bag as the inner bag liner is automatically gradually unfolded or stretched by the output from the stoma first contacting the bottom of the inner bag liner and pressing the same down into the receiving bag.

The inner bag liner may be provided with at least one folding line for compacting the bag lengthwise. The folding lines may form at least one bellow, which ensures that output from the stoma is disposed directly to the bottom of the inner bag liner causing an unfolding only exposing the sides thereof after filling the lower parts which reduces the risk of adherence to the sides of the inner bag liner.

In another embodiment of the invention the folding lines form a telescopic bellows giving a relatively narrow front when the inner bag liner expands into the receiving member.

The folding lines may form spiral lines when compacting the bag lengthwise, e.g. while rotating the inner bag liner along its lengthwise axis.

For keeping the disc-shaped member in a compact conformation, for easy handling and for protecting the inner bag liner before use it is suitable to provide the closed end of inner bag liner in a compacted state is provided with a cover.

The cover and the first annular flange may be situated in substantially the same plane. In some embodiments the plane of the cover and the plane of the annular flange are substantially parallel and the two planes are provided with a distance of a few millimeters, such as between 0.5 and 3 millimeters, or between 1 and 2 millimeters.

The inner bag liner of the present invention may be provided with a membrane being permeable to intestinal gas and impermeable to liquids. Such a membrane could be provided in the first flange or alternatively in the second flange or on any part of the receiving member or the inner bag liner.

In a THIRD ASPECT the present invention relates to an ostomy appliance comprising, a base plate having a third hole for receiving a stoma, ureter, or catheter and an adhesive wafer having a inner surface to be attached to the wearer's abdomen, back, or chest; a receiving member adapted to be releasably attached to the base plate, said member having a second hole for receiving wastes exiting the stoma, ureter or catheter, and a disposable inner bag liner according to any of first and/or second aspect of the present invention, the inner bag liner forming a bag inside the receiving member.

The outer diameter of the first flange may be greater than the inner diameters of the second flange and a third flange defined by the base plate. Thus an overlap between the first flange and both the second and third flanges is provided. If the flanges are adhered to each other it is not possible for waste material to by pass the ostomy appliance and leave spots on the clothes of the user. In this way it is possible to ensure that the waste material enters the inner bag and is kept in said bag.

In one embodiment the second surface of the first flange and the second flange are adapted to be adhered to each other with a first peel strength, and the second flange and a third surface of the base plate are adapted to be adhered to each other with a second peel strength and wherein the first peel strength is bigger that the second peel strength. In another embodiment the first peel strength is lower than the second peel strength. Thus it is possible to remove the receiving member without removing the inner bag liner from the base plate. While the outer member is removed it is possible to apply a new inner bag liner to the receiving member. At the same time the inner bag liner is applied to the base plate and thus any waste material exiting the stoma will be collected by the inner bag liner which is still applied to the base plate. When the new inner bag liner has been applied to the receiving member the old inner bag liner may be removed and the receiving member with the new inner bag liner may be applied quickly. Thus the period without an inner bag liner adhered to the base plate is as short as possible.

According to a FOURTH ASPECT the present invention relates to a method of applying to an inner bag liner according to any combination of features and/or elements the aforementioned aspects, a receiving member according to any combination of features and/or elements the aforementioned aspects. The method includes providing the inner bag liner, removing a release liner from the second surface of the first flange of the inner bag liner, placing the first alignment element in relation to the second flange of the receiving member, and adhering the second surface of the first flange of the inner bag liner to the surface of the second flange of the receiving member.

The first surface may be provided with an adhesive and thus make it possible to adhere the first flange of the inner bag liner to the second flange of the receiving member.

In one embodiment, the step of placing the first alignment element includes the steps of placing the geometrical shape of the first flange in relation to a corresponding geometrical shape of the second flange. For example, if the first alignment element is provided as a line on the release liner, the release liner is placed such that the line coincides with a shape of the second flange. The geometrical shape of the release liner may have a shape which is substantially identical to the outer rim of the second flange. Thus the release liner may be placed such that a line on the release liner coincides with the outer rim of the second flange of the receiving member.

In another embodiment the step of placing the first alignment means comprises the steps of; bringing the first alignment surface of the first alignment means into contact with the second surface of the second alignment means. Thus if the release liner is provided with a hole to be engaged by a protrusion or a tap of the second flange the hole is lowered over the protruding element. I.e. the protruding element or tap is inserted into the hole. If the release liner is provided with an alignment leg along the entire rim, the release liner is placed over the second flange and the alignment leg will be brought into contact with the edge of the second flange.

Furthermore, the method may comprise the steps of: prior to providing the inner bag, locating the stoma and applying the base plate according to the third aspect of the invention; and after adhering the second surface of the first flange to the surface of the second flange, removing the release liner from the first adhesive surface of the first flange of the inner bag liner and attaching the receiving member and the inner bag liner to the base plate.

Features and elements of the first, second, third and fourth aspect of the present invention may be combined in any way.

These and other objects of the invention, as well as many of the intended advantages thereof, will become more readily apparent when reference is made to the following description taken in conjunction with the accompanying drawings.

DETAILED DESCRIPTION OF THE INVENTION

Figure 2:
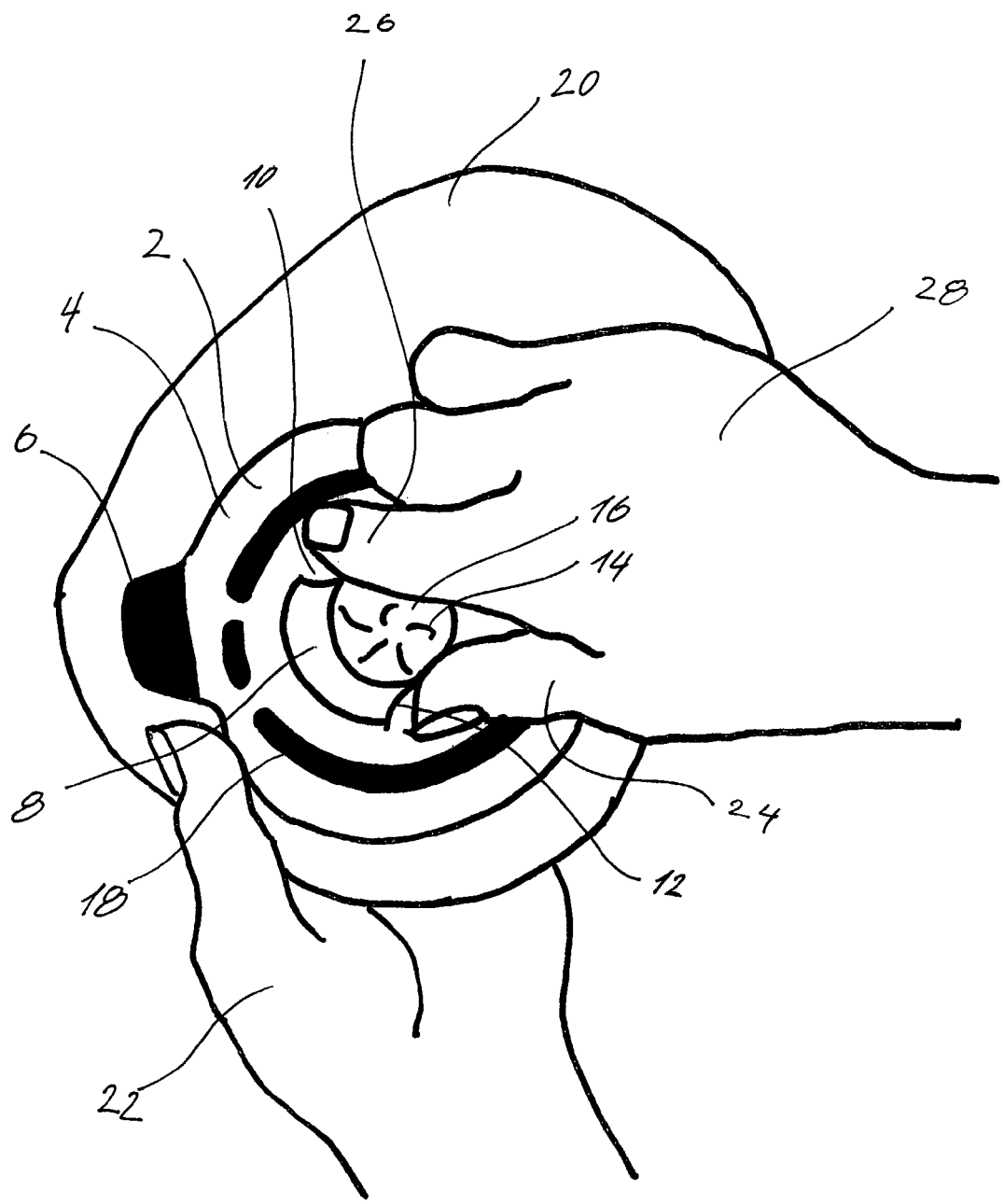
Figure 3:
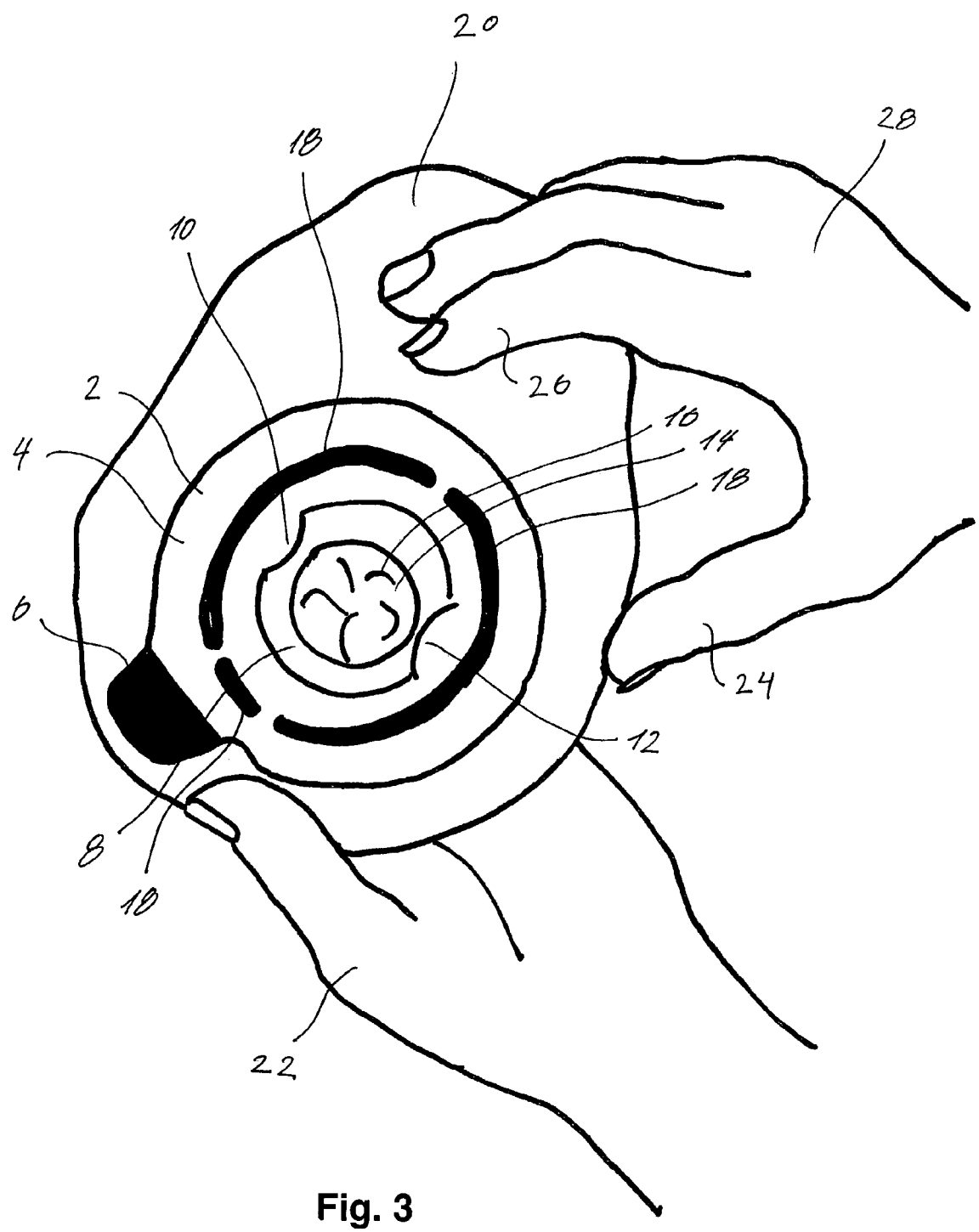
Figure 7:
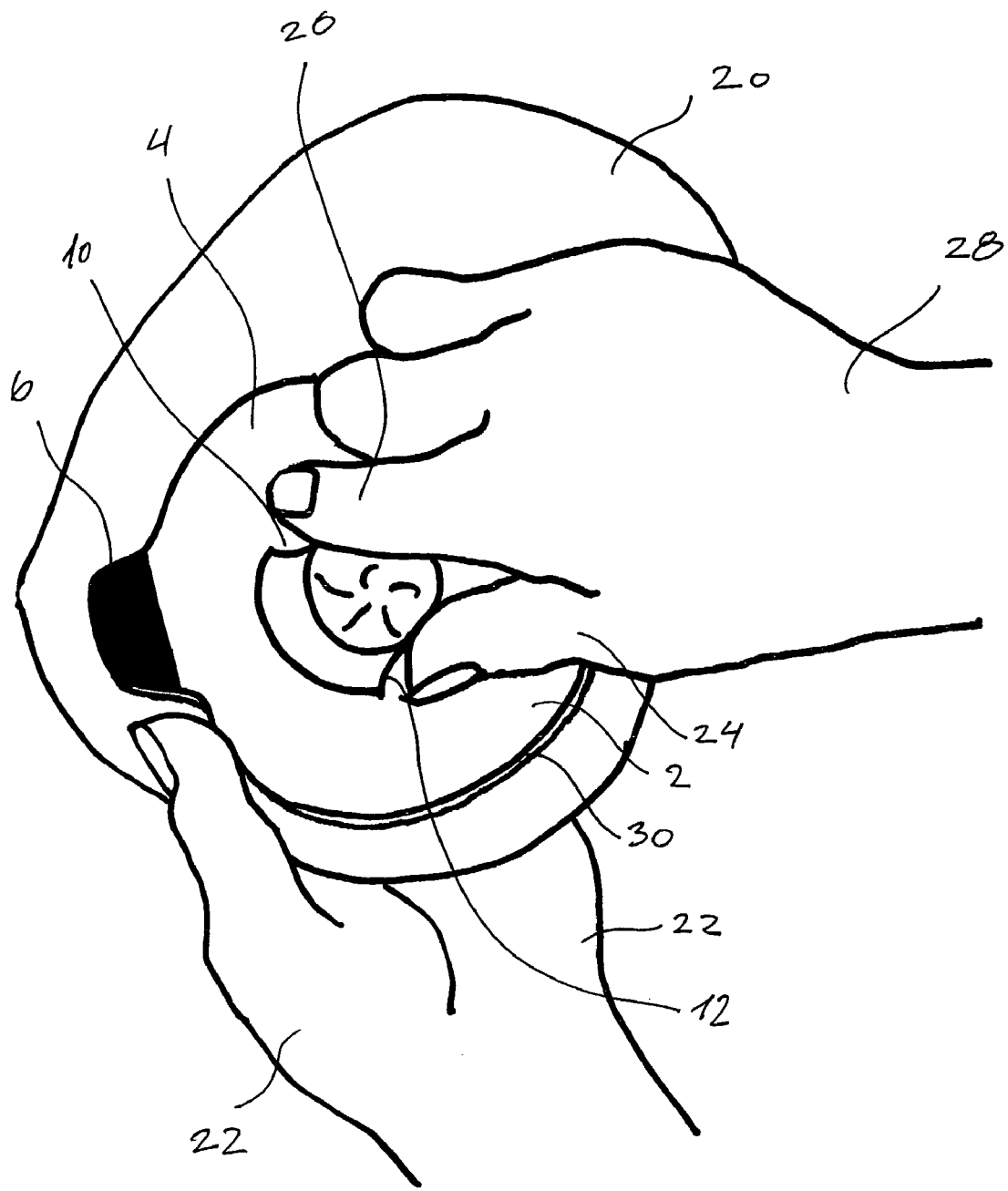
Figure 8:
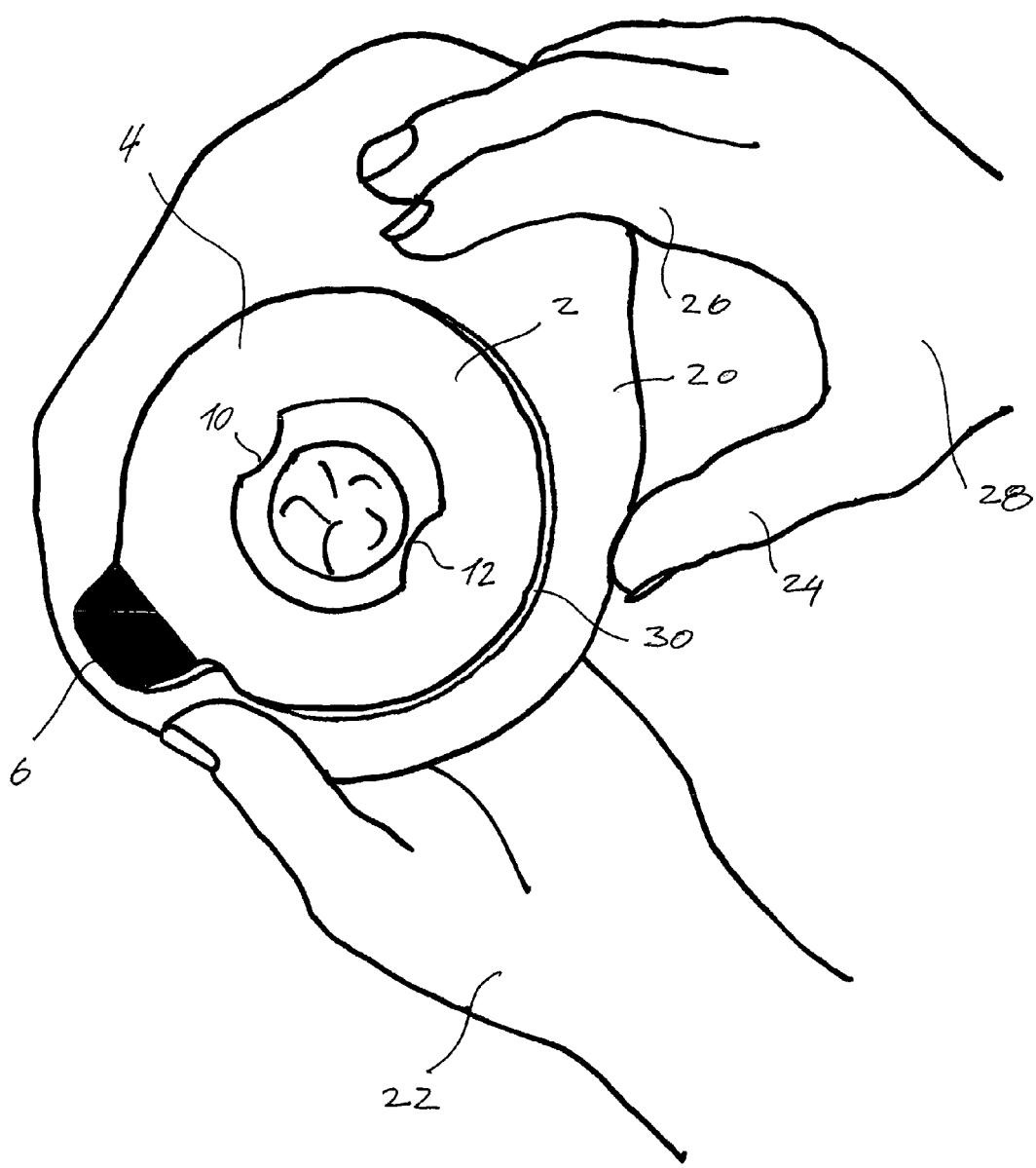
Figure 9:
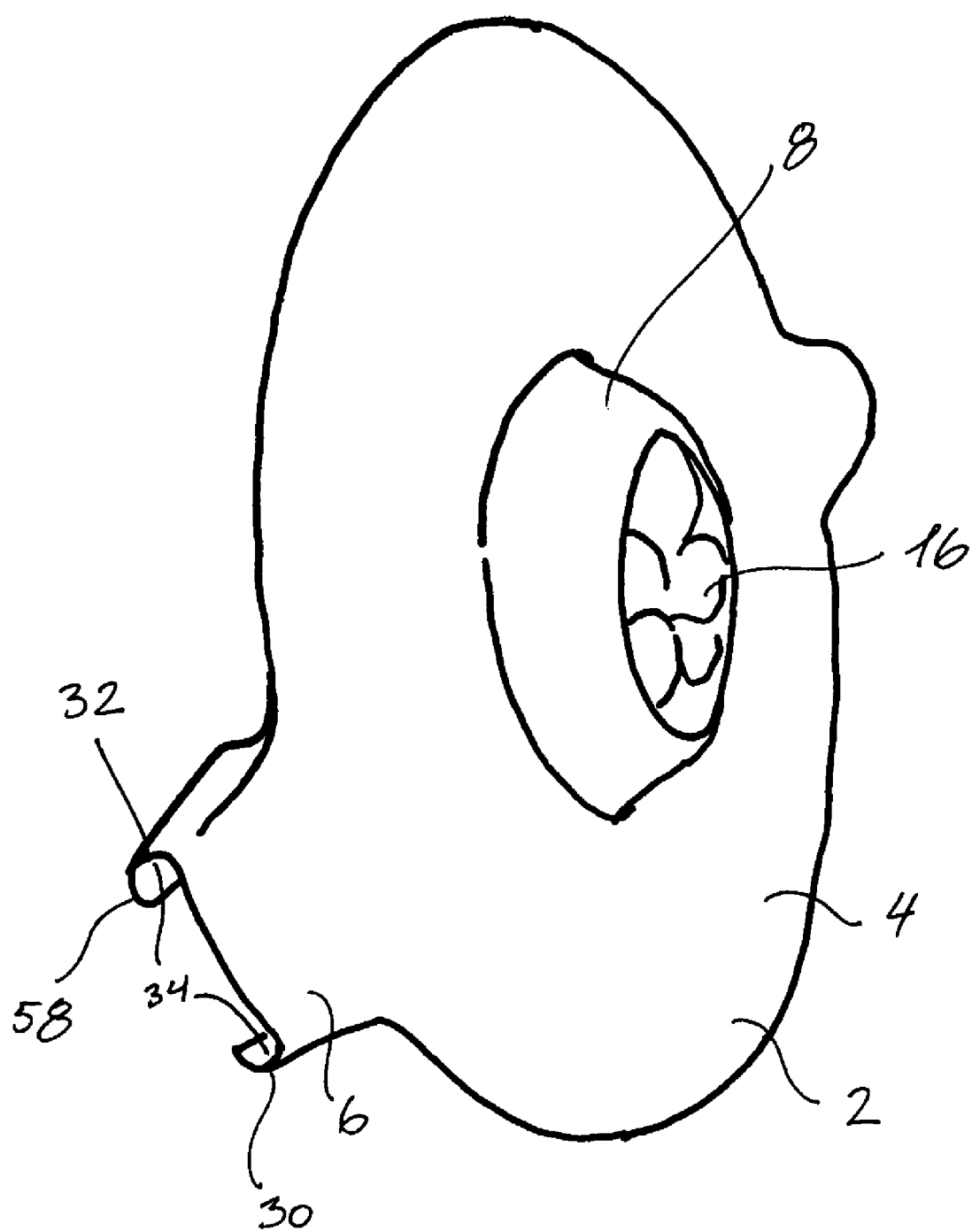
Figure 10:
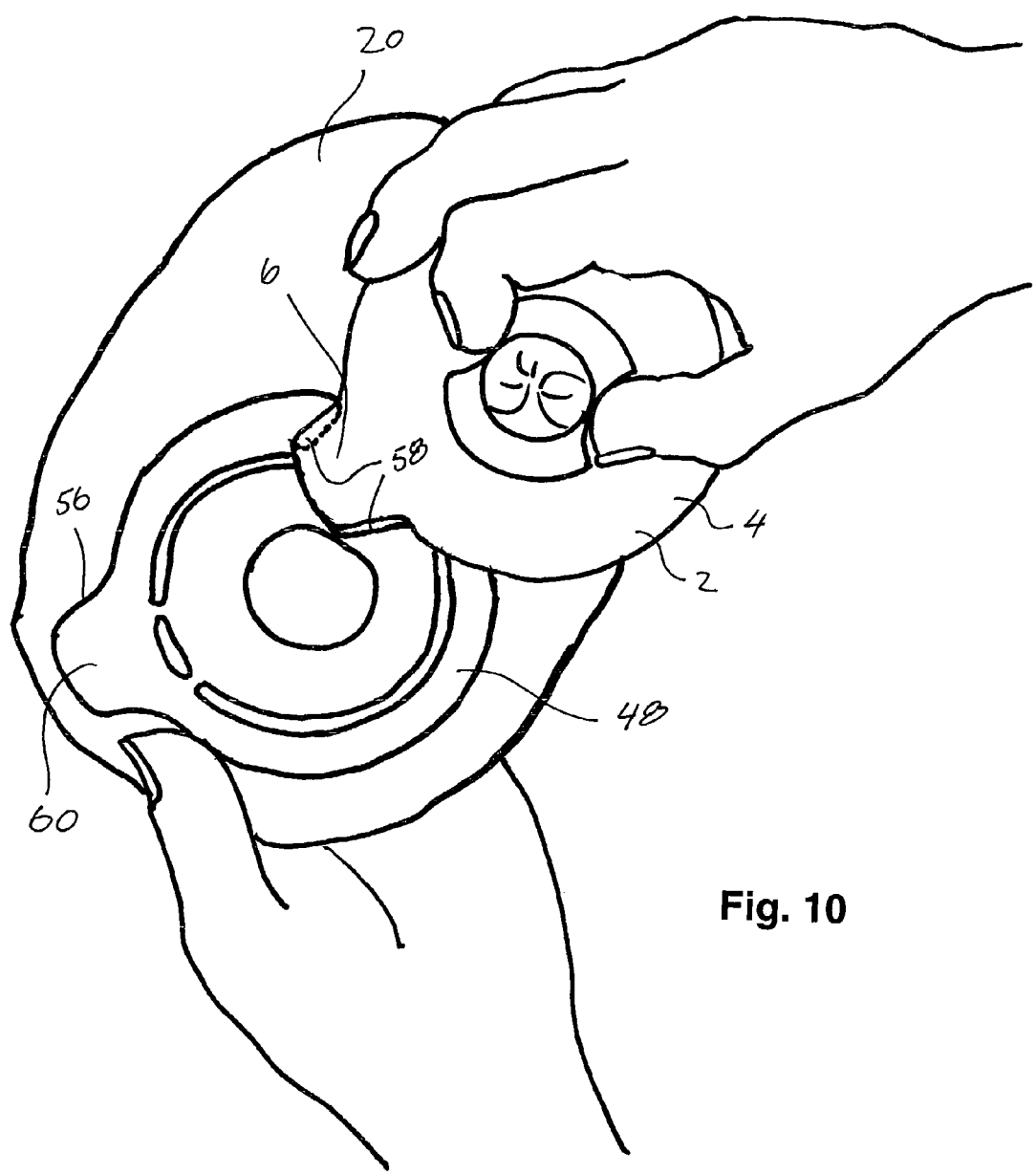
Figure 11:
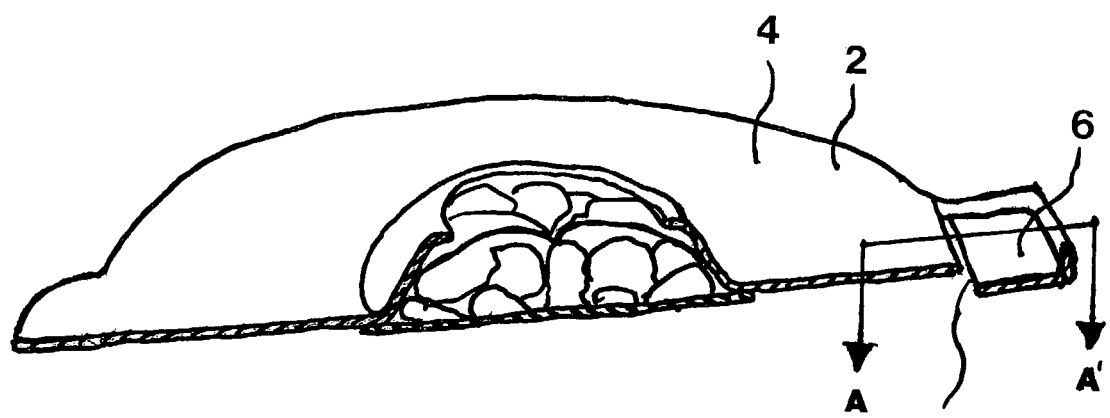
Figure 11:
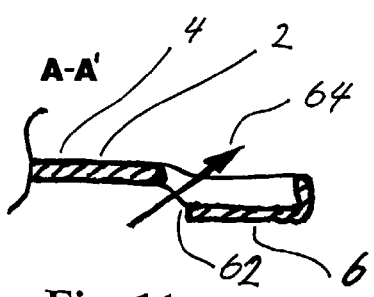
Figure 12:
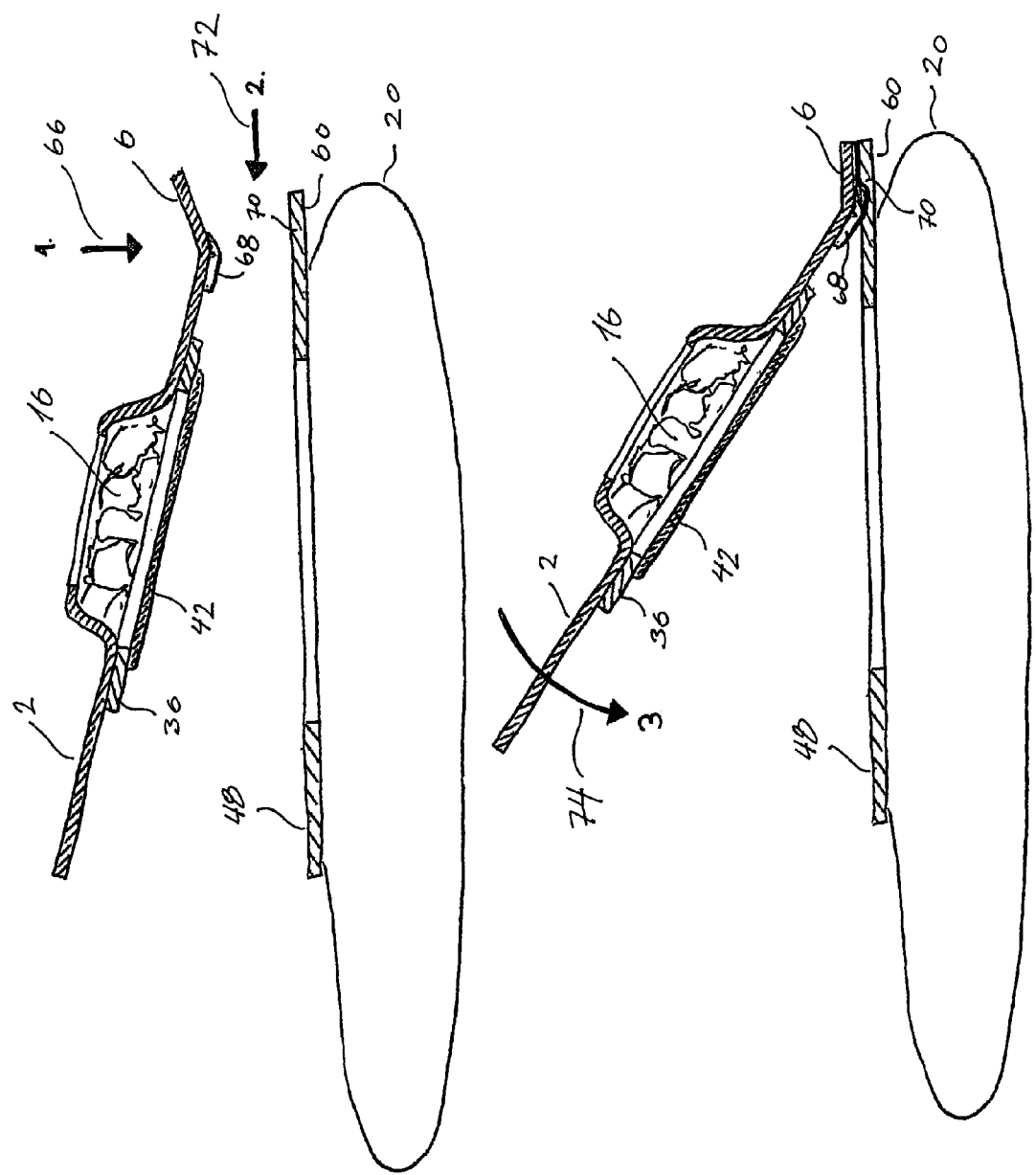
Figure 13:
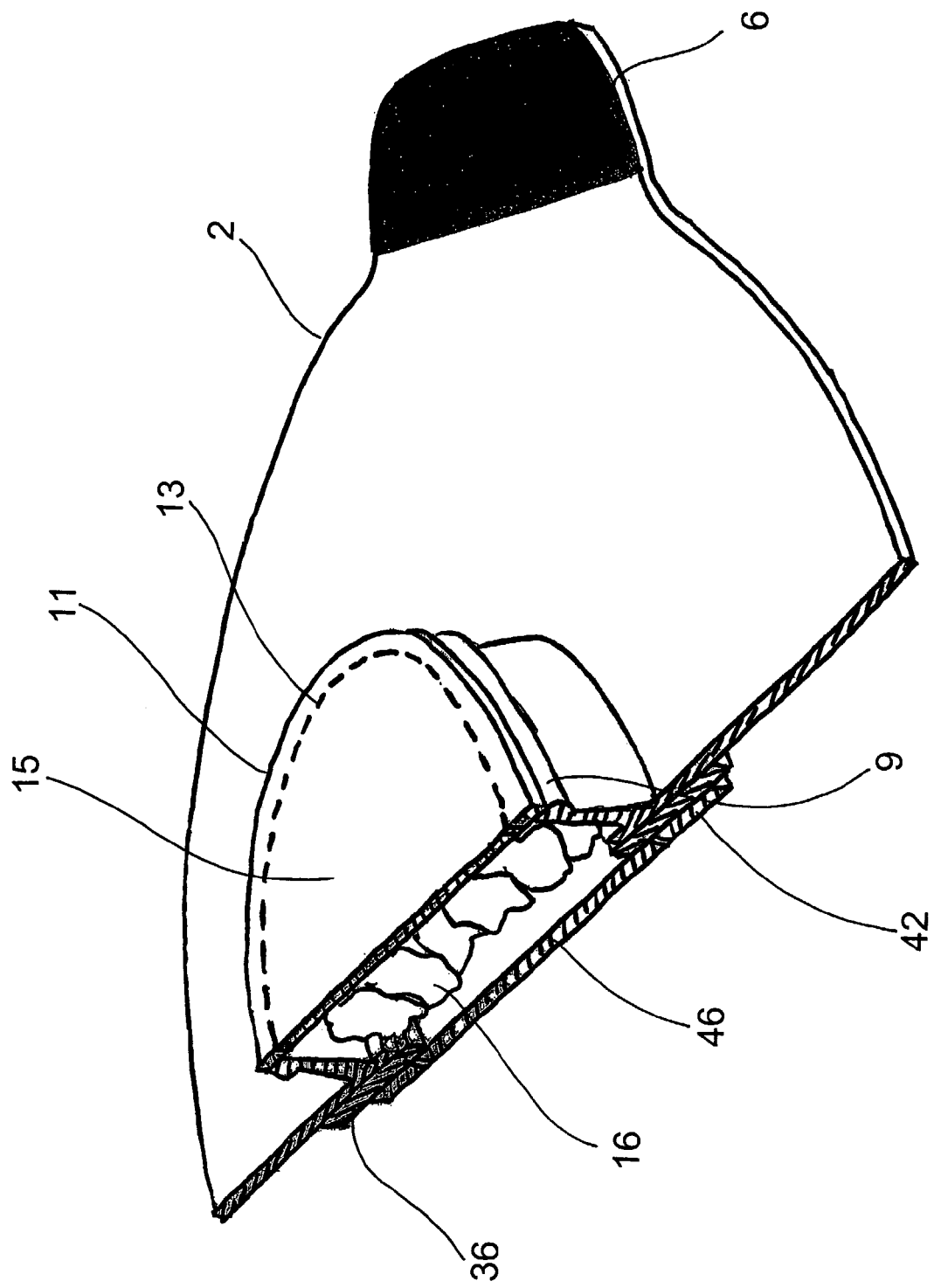
Figure 14:
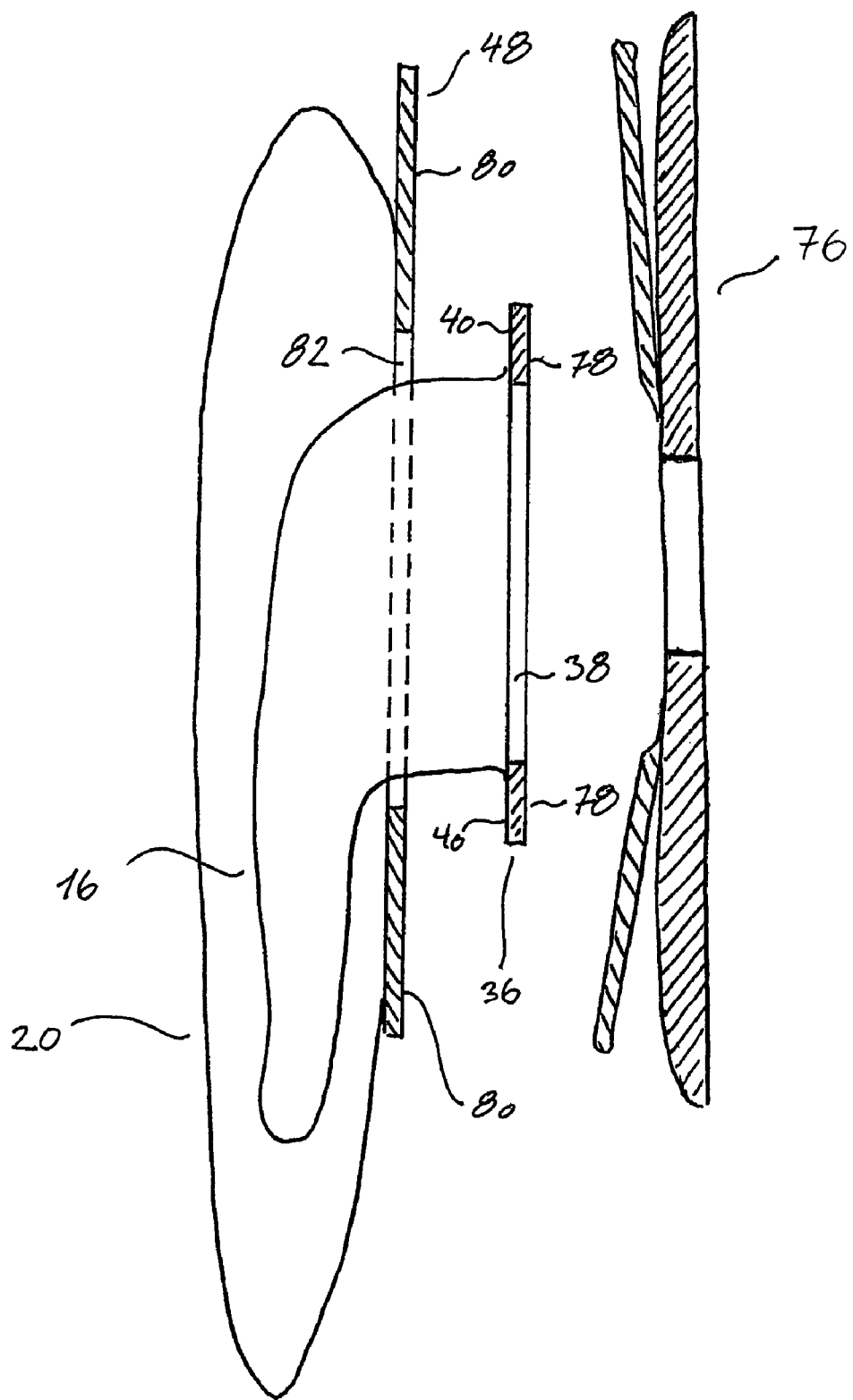
Figure 15:
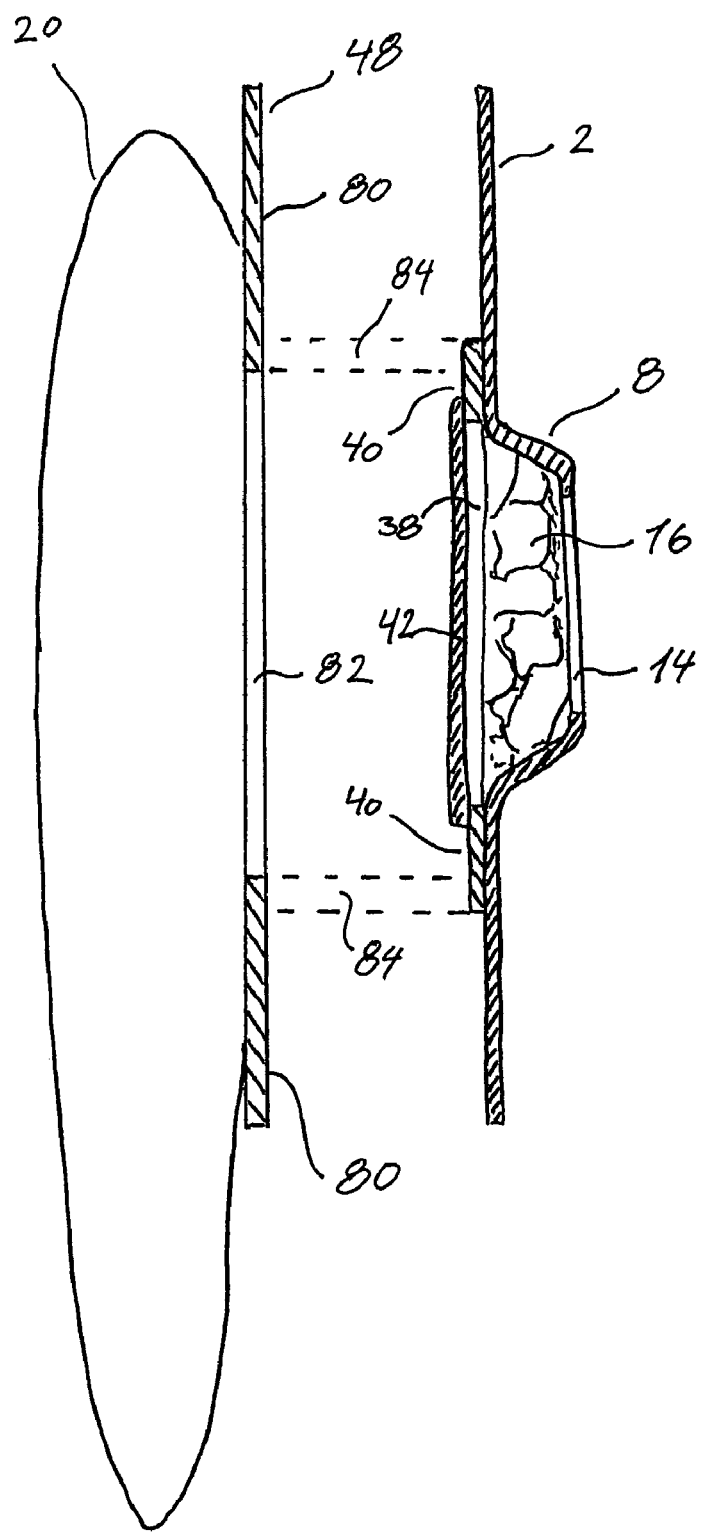

Embodiments of the invention will now be described in details with reference to the drawing in which:

FIGS. 1-3 show a release liner with a line aiding correct application of an inner bag liner, FIGS. 4-8 show a release liner with an alignment leg along the entire rim, FIGS. 9-10 show a release liner with an alignment leg on a projecting part of the release liner, FIGS. 11a-11b show a release liner with an alignment recess in a projecting part of the release liner, FIG. 12 shows a release liner with a part projecting from the central part, FIG. 13 shows a release liner with a protection film, and FIGS. 14 and 15 show the general principle of the inner bag liner with the release liner, the receiving outer bag and the base plate.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BEST MODE OF CARRYING OUT THE INVENTION

FIG. 1 shows a release liner 2 comprising a central portion 4 and a gripping means 6. The gripping means is provided as a tap protruding from the central portion 4. The release liner 2 is provided with a compartment 8 comprising first gripping surface 10 and second gripping surface 12. The gripping surfaces are placed opposite each other and may be gripped with a thumb and an index finger. The compartment is provided with a hole 14 through which a finger may push the inner bag liner 16 (in FIG. 1 provided in the compacted state) into the receiving member (not shown). The release liner is provided with a geometrical shape in the form of a line 18 having a shape similar to a recess in the second flange of the receiving member.

FIGS. 2 and 3 show the placement of the release liner 2 (and the inner bag liner) on a receiving member 20. In the figure the receiving member 20 is held by left hand 22 and the release liner is gripped by means of thumb 24 and index finger 26 of the right hand 28. Naturally the release liner may be held by the left hand and the receiving member may be held by the right hand. The thumb 24 is pressed against the second gripping surface 12 and index finger 26 is pressed against first gripping surface 10. When placing the release liner on the receiving member 20 the user can use the line 18 to coincide the release liner correctly as the line 20 has a shape identical to a recess of the second flange (not shown).

Figure 4:
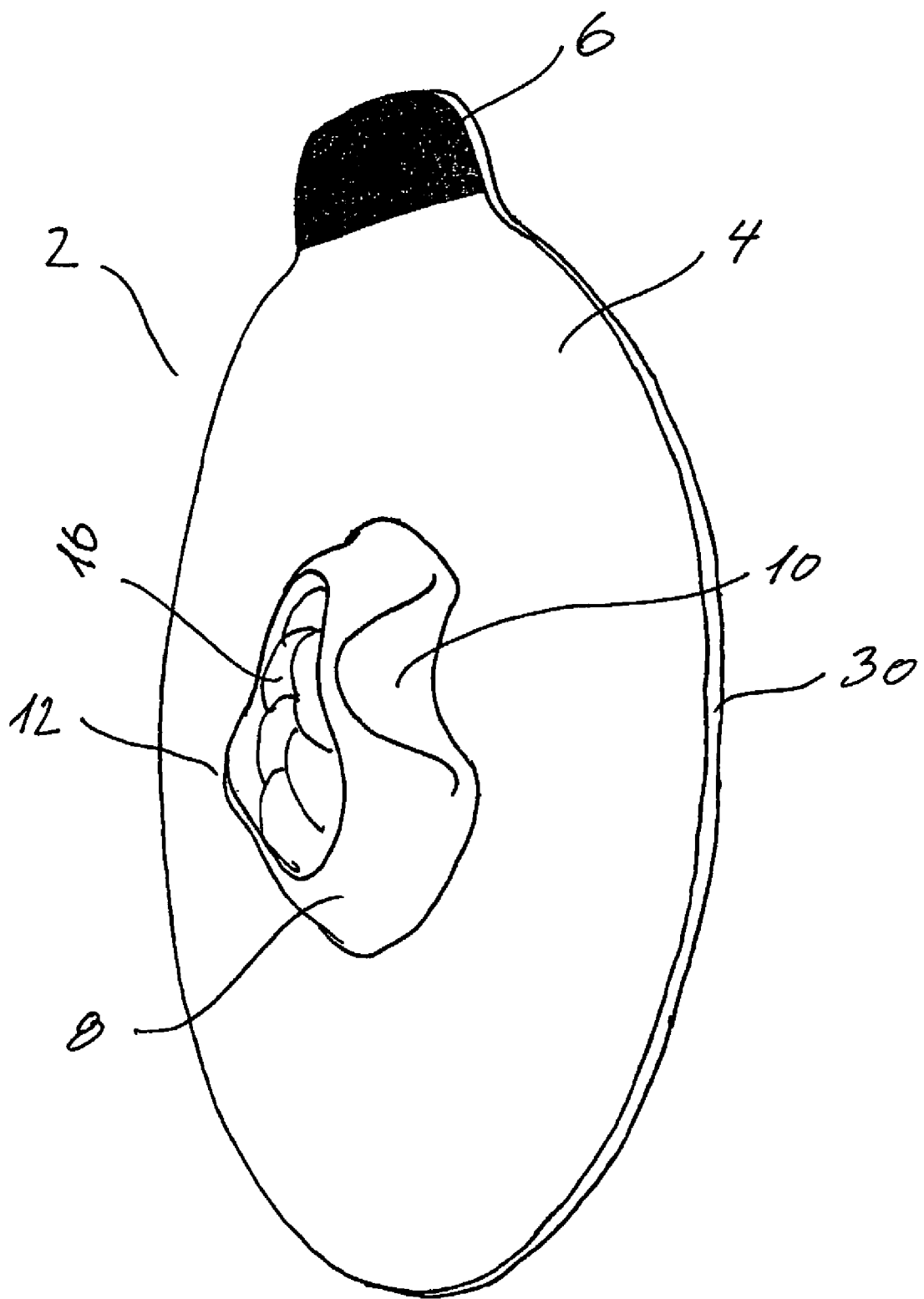
Figure 5:
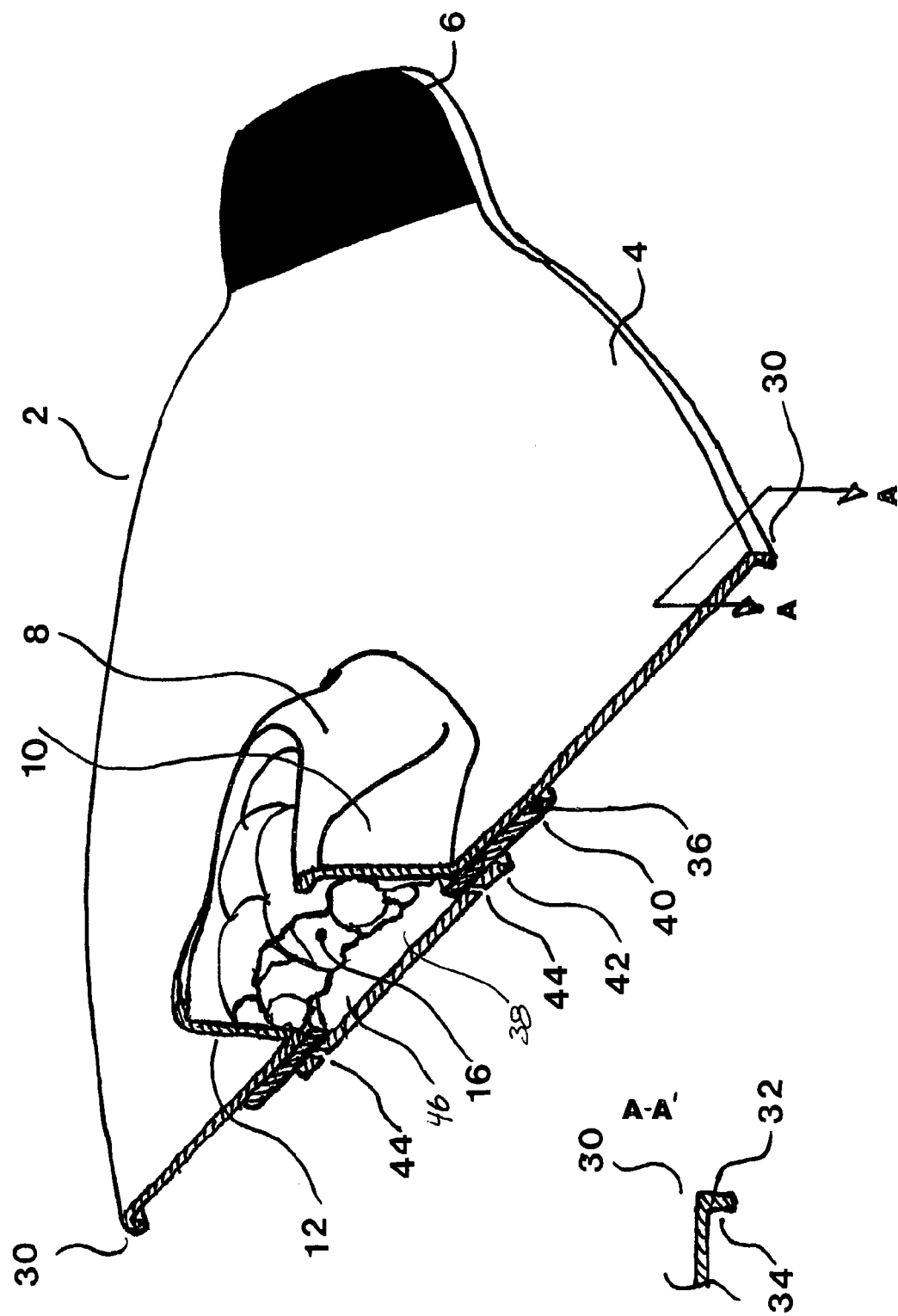

FIGS. 4, 5a and 5b show a release liner 2 comprising a central portion 4 and a gripping element 6 in the form of a tap. The release liner is provided with first gripping surface 10 and second gripping surface 12 provided on compartment 8. An inner bag liner 16 is provided in the compacted state in the compartment 8. The release liner 2 is furthermore provided with an alignment leg 30. The alignment leg has a transversing part 32 comprising a first engagement surface 34. The engaging surface 34 is adapted to engage an outer rim 56 of the second flange of the outer receiving member (see FIG. 6). The inner bag liner 16 comprises a first flange 36 having a first hole 38 and a second surface 40 to be adhered to the second flange of the receiving member. Opposite the second surface 40 is provided the first surface 78 of the first flange (see FIG. 14) which is adhered to the release liner 2 (see FIG. 15). A cover 42 is provided over the hole 38. The cover comprises a first perforated line 44 which encircles a first removable part 46. When the first flange 36 is adhered to the second flange the inner bag liner 16 may be pushed into the receiving member and when this is done the first removable part 46 (or at least a part of it) is detached from the rest of the cover. As the cover 42 is provided next to the first flange 36, the cover 42 and the flange 36 are substantially in the same plane. Once the inner bag liner has been pushed into the receiving member, the release liner 2 may be removed to adhere the first surface 78 of the first flange 36 to the base plate 76 (see FIG. 14), with the base plate being adhered to the skin of the user.

Figure 6:
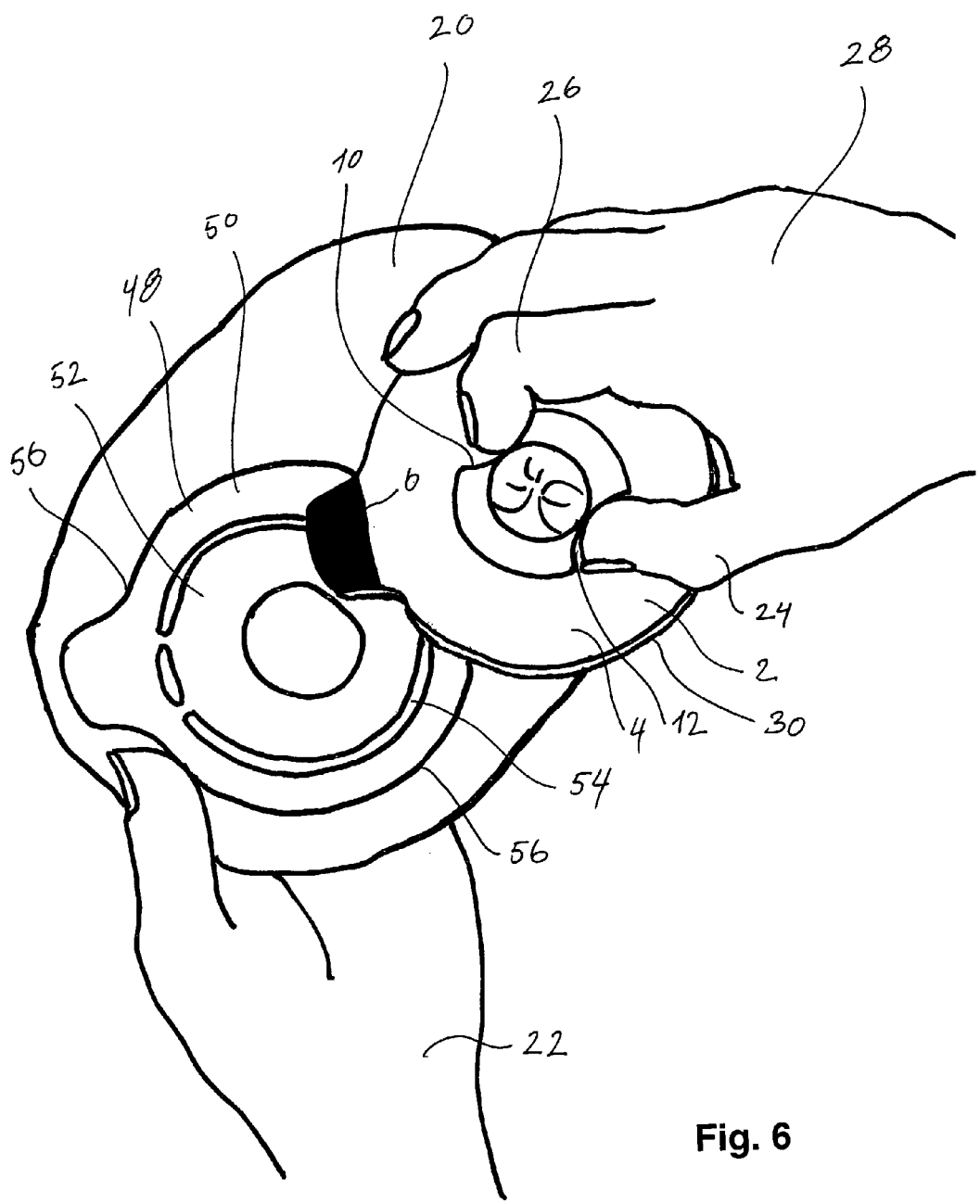

FIGS. 6-8 show how the first flange 36 (shown in FIGS. 12-15) is placed in relation to the second flange 48. The second flange 48 comprises an outer flange part 50 and an inner flange part 52. The two parts are separated by a recess 54. The inner flange part 52 is to be attached to the first flange of the inner bag liner and the outer flange part 54 is to be attached to a base plate which is adhered to the skin of the user. The user may hold the receiving member 20 with the left hand 22 and grip the release liner 2 by means of thumb 24 and index finger 26 of the right hand 28. As the release liner 2 is provided with an alignment leg 30 the task for the user is now to align the release liner such that the first engagement surface 34 (see FIG. 5b) of the release liner is in contact with the outer rim 56 of the second flange. As the first flange is provided with gripping means 6 which extends from the central portion 4, it is only possible to position/align the release liner in one way.

In FIGS. 9-10 are shown a different embodiment of the present invention. The release liner 2 is provided with a compartment 8 and a central portion 4 and a gripping means 6. The gripping means is provided with an alignment leg comprising a transversing part 32 and parallel part 58. The gripping part is used to align the release liner in relation to the second flange 48 as the gripping part 6 is pulled in over a corresponding tap 60 of the second flange 48. By doing this the first engagement surface 34 of the release liner 2 is brought into contact with the outer rim 56 of the tap 60. At the same time the tap is trapped between the parallel part 58 and the release liner and the release liner (and thereby also the first flange) is positioned correctly in relation to the second flange 48.

A further alternative is shown in FIGS. 11a and 11b, wherein the release liner 2 comprises central part 4 and a gripping/alignment part 6. A positioning recess 62 is provided in the gripping part 6 which serves as a first alignment element. When the release liner is to be positioned correctly in relation to the second flange, the tap 60 of the second flange 48 (see FIG. 10), which acts as a second alignment element, is inserted into the recess 62, as indicated by arrow 64. The gripping part 6 is parallel to the base part 4 of the release liner but the two parts are provided spaced apart such that the planes of the two parts (4 and 6) are parallel but do not coincide—this may be seen in FIG. 11b.

In FIG. 12 is seen a receiving bag 20 having a second flange 48 and an inner bag liner 16 having a first flange 36 to which a cover 42 is attached. The inner bag liner 16 is adhered to a release liner 2 having a central part 4 and a gripping means 6. When the first flange 36 of the inner bag liner 16 is to be adhered to the second flange 48 of the receiving bag 20, the first alignment element 68 of the release liner 2 is brought into contact with a tap 60 of the second flange 48 which acts as a second alignment element. The movement is indicated by arrow 66. In order to bring the first alignment element 68 in contact with the edge 70 of the tap 60, the release liner 2 is moved as indicated by arrow 72. When contact is made the release liner is placed such that when rotating the release liner as indicated by arrow 74, the first flange and the second flange are aligned correctly and the first flange is retained in a direction substantially parallel with the second flange.

FIG. 13 shows the release liner 2 with the compartment 8 defining the gripping area, meaning the outer surface of the compartment 8. The compartment 8 comprises a projecting rim 9 at the distal part of the compartment in relation to the first flange 36 of the inner bag liner 16 for improved gripping of the release liner. The release liner 2 is provided with a protection film 11 placed at the opposite side of the release liner in relation to the cover 42. The protection film 11 comprises a second perforated line 13 which encircles a second removable part 15.

In FIGS. 14 and 15 are shown the general principle of the inner bag liner 16 with the release liner 2, the outer receiving member 20 and a base plate 76. In FIG. 15 the inner bag liner 16 is shown in the compacted state and in FIG. 14 it is shown in the unfolded state. The inner bag liner 16 comprises a first flange 36 having a first hole 38, a first surface 78 and a second surface 40. The second surface 40 is to be adhered to an outer surface 80 of the second flange 48 of receiving member 20. The second flange 48 comprises a second hole 82. When the inner bag liner 16 is being applied to the receiving member 20, the first surface 78 of the first flange 36 is covered by the release liner 2 as shown in FIG. 15. This allows the alignment element to be used to align the first flange with the second flange of the receiving member. When the first flange 36 is attached to the second flange 48, having been properly aligned using the alignment element on the release liner 2, an overlap 84 is provided between the flanges. The release liner 2 comprises a compartment 8 having a hole 14. A cover 42 is provided over the hole 38. Once the first flange 36 is adhered to the second flange 48, a user may force the inner bag liner 16 into the outer receiving member 20 by inserting a finger into the hole 14. Such insertion of a finger will cause the cover 42 to rupture and the inner bag liner 16 to be forced into the outer receiving member 20. The release liner 2 may then be removed, leaving the first surface 78 of the first flange ready for adherence to the base plate 76, as shown in FIG. 14.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A disposable inner bag liner for an ostomy appliance applied to a human body, the inner bag liner being capable of forming a bag inside an outer receiving member, said outer receiving member having a hole for receiving a stoma, ureter, or catheter for receiving effluents or waste products of the body, and a flange, said disposable inner bag liner comprising:

an open end having an annular flange that includes a hole for receiving a stoma, ureter, or catheter for receiving effluents or waste products of the body, a first surface being provided with an adhesive and a release liner, and a second surface;

said outer receiving member flange and the second surface of the liner being adapted to be releasably adhered to each other;

said release liner on said first surface including a first alignment element for aligning the inner bag liner flange in relation to the outer receiving member flange;

said outer receiving member flange having a second alignment element adapted to cooperate with the first alignment element of the release liner such that the inner bag liner flange is retained in a direction substantially parallel with said outer receiving member flange; and said release liner being removed prior to adhering said bag liner first surface to a base plate on a user.

2. The disposable inner bag liner according to claim 1, wherein the first alignment element is adapted to align the hole in the inner bag liner to be substantially concentric in relation to the hole in the outer receiving member.

3. The disposable inner bag liner according to claim 1, wherein the first alignment element is adapted to align the flange on the inner bag liner to be substantially concentric in relation to the flange on the outer receiving member.

4. The disposable inner bag liner according to claim 1, wherein the first alignment element on the release liner is adapted to engage the second alignment element on the outer receiving member.

5. The disposable inner bag liner according to claim 1, wherein the first alignment element on the release liner defines a protrusion on a first alignment surface.

6. The disposable inner bag liner according to claim 1, wherein the first alignment element on the release liner defines a recess and/or hole adapted to be engaged by the second alignment element on the outer receiving member.

7. The disposable inner bag liner according to claim 1, wherein the second alignment element on the outer receiving member defines a recess and/or hole adapted to be engaged by the first alignment element on the release liner.

8. The disposable inner bag liner according to claim 1, wherein the first alignment element on the release liner defines an alignment leg that protrudes from at least a part of an outer rim of the flange on the inner bag liner and/or the release liner.

9. The disposable inner bag liner according to claim 8, wherein the alignment leg protrudes along the entire outer rim of the flange on the inner bag liner.

10. The disposable inner bag liner according to claim 1, wherein the first alignment element on the release liner has a geometrical shape indicating a corresponding shape of the flange on the outer receiving member.

11. The disposable inner bag liner according to claim 10, wherein the geometrical shape protrudes from the inner bag liner flange.

12. The disposable inner bag liner according to claim 10, wherein the geometrical shape defines a line on the surface of the inner bag liner flange.

13. The disposable inner bag liner according to claim 1, wherein the release liner includes a gripping element.

14. The disposable inner bag liner according to claim 13, wherein the gripping element protrudes from an outer rim of the release liner.

15. The disposable inner bag liner according to claim 14, wherein a gripping plane defined by at least a part of the gripping element is transverse to a liner plane defined by at least a part of the release liner provided inside the outer rim.

16. The disposable inner bag liner according to claim 15, wherein the gripping plane and the liner plane define an angle of between 5 to 45 degrees.

17. The disposable inner bag liner according to claim 13, wherein the gripping element protrudes from a surface of the release liner.

18. The disposable inner bag liner according to claim 16, wherein the gripping element defines at least two gripping surfaces so as to allow gripping of the release liner with two fingers.

19. The disposable inner bag liner according to claim 18, wherein the gripping surfaces are transverse to a liner plane defined by at least a part of the release liner.

20. The disposable inner bag liner according to claim 18, wherein the gripping surfaces are concave.

21. The disposable inner bag liner according to claim 20, further comprising a compartment projecting from the release liner, the compartment defining the gripping surfaces.

22. The disposable inner bag liner according to claim 1, wherein the closed end of the inner bag liner in a compacted state is provided with a cover.

23. The disposable inner bag liner according to claim 22, wherein the release liner is provided with a protection film placed at an opposite side of the release liner in relation to the cover.

24. A disposable inner bag liner for an ostomy appliance applied to a human body, the inner bag liner being capable of forming a bag inside an outer receiving member, said outer receiving member having a hole for receiving a stoma, ureter, or catheter for receiving effluents or waste products of the body, and a flange, said disposable inner bag liner comprising:
  an open end having an annular flange that includes a hole for receiving a stoma, ureter, or catheter for receiving effluents or waste products of the body, a first surface being provided with an adhesive and a release liner, and a second surface;
  said outer receiving member flange and the second surface of the liner being adapted to be releasably adhered to each other;
  said release liner on said first surface including an alignment element for aligning the inner bag liner flange in relation to the outer receiving member flange;
  said release liner further including a compartment projecting therefrom that defines a gripping element having at least two gripping surfaces to allow gripping of the release liner with two fingers; and
  said release liner being removed prior to adhering said bag liner first surface to a base plate on a user.

25. The disposable inner bag liner according to claim 24, wherein the gripping element protrudes from an outer rim of the release liner.

26. The disposable inner bag liner according to claim 24, wherein the gripping surfaces are transverse to a liner plane defined by at least a part of the release liner.

27. The disposable inner bag liner according to claim 24, wherein the gripping surfaces are concave.

* * * * *